United States Patent [19]

Smith et al.

[11] Patent Number: 5,047,577

[45] Date of Patent: Sep. 10, 1991

[54] QUATERNARY AMMONIUM COMPOUNDS

[75] Inventors: Kim R. Smith; Joe D. Sauer; James E. Borland, all of Baton Rouge, La.

[73] Assignee: Ethyl Corporation, Richmond, Va.

[21] Appl. No.: 894,938

[22] Filed: Aug. 8, 1986

Related U.S. Application Data

[63] Continuation of Ser. No. 782,353, Oct. 1, 1985, Pat. No. 4,883,917.

[51] Int. Cl.$^5$ .............................................. C07C 67/02
[52] U.S. Cl. .................................. 560/253; 560/250; 252/186.1
[58] Field of Search ............................... 560/250, 253; 252/186.1

[56] References Cited

U.S. PATENT DOCUMENTS

| | | | |
|---|---|---|---|
| 2,295,504 | 9/1942 | Shelton | 560/250 U X |
| 2,380,877 | 7/1945 | Shelton | 560/250 X |
| 2,541,248 | 2/1951 | Hibbs . | |
| 3,557,214 | 1/1971 | Koenig et al. | 560/250 X |
| 4,313,889 | 2/1982 | Bodor | 560/250 X |
| 4,470,918 | 9/1984 | Mosier | 560/155 U X |

Primary Examiner—Paul F. Shaver
Attorney, Agent, or Firm—Joseph D. Odenweller; John F. Sieberth

[57] ABSTRACT

Peroxygen laundry bleach (e.g. sodium perborate) is activated to be effective at a lower temperature by use in combination with a hydrocarbonyloxyhydrocarbyl trihydracarbyl quaternary ammonium salt, e.g. dodecyldimethyl 2-acetyloxyethylammonium bromide.

21 Claims, No Drawings

QUATERNARY AMMONIUM COMPOUNDS

This application is a continuation-in-part of Application Ser. No. 782,353, filed Oct. 1, 1985, now U.S. Pat. No. 4,883,917.

BACKGROUND OF THE INVENTION

Bleach is commonly used to whiten soiled fabrics during laundry operations. The most common bleach is aqueous sodium hypochlorite referred to as chlorine bleach. Chlorine bleach is effective and cheap but has certain disadvantages. It cannot be mixed with the detergent in a single package. It tends to attack certain dyes and also degrades fabrics. In addition, fabrics having a resin finish (wash and wear fabrics) are given a noticeable yellow tint by chlorine bleach.

In order to overcome these disadvantages, another class of laundry bleach has come into use. This class is referred to as peroxygen bleach. These materials are very effective whitening agents and are much safer with dyed fabrics. In addition they do not yellow wash and wear fabrics. Many can be packaged together with a detergent and other components to form a single detergent-bleach laundry package.

Although peroxygen bleaches have these many attributes, they have several drawbacks. They are more expensive compared to chlorine bleach and also are not effective unless the wash solution is at a temperature high enough to activate the peroxygen compound. For example, sodium perborate requires a water temperature above about 160.F which is higher than that usually attained in domestic laundry operations. In order to lower the temperature at which peroxygen bleach can be used, resort is had to "bleach activators". These are compounds that by themselves have no bleaching action but when used in combination with a peroxygen bleach form a peroxygen compound which is effective at lower temperatures than the initial peroxygen bleach. Examples of such bleach activators are tetraacetylethylenediamine, sodium p-acetoxybenzene sulfonate and sodium p-heptanoyloxybenzene sulfonate.

SUMMARY OF THE INVENTION

It has now been discovered that certain trihydrocarbylhydrocarbonyloxyhydrocarbyl ammonium quaternary ammonium salts are effective activators for peroxygen bleaching compounds capable of forming hydrogen peroxide in aqueous solutions.

DESCRIPTION OF THE PREFERRED EMBODIMENTS

A preferred embodiment of the invention is an oxygen bleaching composition comprising a peroxygen bleaching compound and a bleach activator having the formula

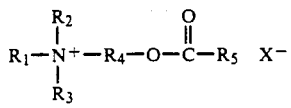

wherein $R_1$, $R_2$ and $R_3$ are aliphatic hydrocarbon groups containing 1-30 carbon atoms, $R_4$ is a divalent aliphatic hydrocarbon group containing 1-12 carbon atoms and $R_5$ is a hydrocarbon group containing 1-20 carbon atoms and X is a monovalent anion.

Some examples of the novel bleach activators are
dodecyldimethyl 2-octadeconyloxyethylammonium bromide;
triacontyldecylmethyl 3-eicosonyloxypropylammonium chloride;
tetracontyldodecylethyl 2-hexadeconyloxybutylammonium iodide;
hexadecyldiethyl 8-dodeconyloxyoctylammonium fluoride;
dihexadecylmethyl 10-nonanoyloxydodecylammonium chloride;
dodecyldimethyl 2-benzoyloxyethylammonium bromide;
dioctylethyl 2-phenylacetyloxypropylammonium chloride; and the like.

Another preferred embodiment consists of bleach activators of the above formula wherein $R_1$ is an alkyl containing 8-20 carbon atoms, $R_2$ is an alkyl containing 8-20 carbon atoms or is a methyl group, $R_3$ is methyl, $R_4$ is the group $-(CH_2)_m-$ wherein m is an integer from 1 to 6, $R_5$ is an alkyl containing 1-6 carbon atoms and X is a monovalent anion. Some examples of these activators are:

octyldimethyl 2-acetyloxyethylammonium chloride;
octadecyldimethyl 3-propionyloxypropylammonium iodide;
dioctylmethyl 3-acetyloxyhexylammonium bromide;
didecylmethyl 2-acetyloxyethylammonium bromide;
decyldimethyl 2-acetyloxyethylammonium chloride;
octyldimethyl 2-acetyloxyethylammonium chloride;
dioctylmethyl 2-acetyloxyethylammonium bromide;
dodecyldimethyl 2-acetyloxyethylammonium bromide;
tetradecyldimethyl 2-acetyloxyethylammonium bromide;
octadecyldimethyl 2-acetyloxyethylammonium chloride; and the like.

A highly preferred embodiment of the invention is a bleach activator wherein $R_1$ is an alkyl containing 8-20 carbon atoms, $R_2$ is an alkyl containing 8-20 carbon atoms or is a methyl group, $R_3$ is methyl, $R_4$ is $-(CH_2CH_2)-$, $R_5$ is an alkyl containing 1-20 carbon atoms and X is halogen. Some examples of this embodiment are:

dioctylmethyl 2-acetyloxyethylammonium chloride;
decyloctylmethyl 2-propionyloxyethylammonium bromide;
dodecyleicosylmethyl 2-eicosonyloxyethylammonium iodide;
octadecyldimethyl 2-octadeconyloxyethylammonium chloride;
eicosonyldimethyl 2-acetyloxyethylammonium bromide;
hexadecyloctylmethyl 2-octanoyloxyethylammonium chloride; and the like.

In a still more preferred embodiment, $R_1$ is an alkyl containing from 8 to 20 carbon atoms, $R_2$ and $R_3$ are methyl, $R_4$ is $-(CH_2CH_2)-$ and $R_5$ is an alkyl containing 1-11 carbon atoms.

Examples of these are:
tetradecyldimethyl 2-acetyloxyethylammonium chloride;
dodecyldimethyl 2-acetyloxyethylammonium chloride;
decyldimethyl 2-acetyloxyethylammonium chloride;
octyldimethyl 2-acetyloxyethylammonium chloride;
eicosyldimethyl 2-dodeconyloxyethylammonium chloride;

octadecyldimethyl 2-nonanoyloxyethylammonium bromide;
hexadecyldimethyl 2-octanoyloxyethylammonium chloride;
dodecyldimethyl 2-decanoyloxyethylammonium iodide; and the like.

Another more preferred embodiment of the invention comprises bleach activators of the above formula in which $R_1$ and $R_2$ are alkyls containing 8-20 carbon atoms, $R_3$ is methyl, $R_4$ is $-(CH_2CH_2)-$ and $R_5$ is an alkyl containing 1-11 carbon Examples of these compounds are:
didodecylmethyl 2-acetyloxyethylammonium chloride;
didecylmethyl 2-acetyloxyethylammonium chloride;
dioctylmethyl 2-acetyloxyethylammonium chloride;
dieicosylmethyl 2-dodecanoyloxyethylammonium chloride;
dioctadecylmethyl 2-decanoyloxyethylammonium bromide;
dodecylhexadecylmethyl 2-nonanoyloxyethylammonium iodide;
didodecylmethyl 2-pentanolyoxyethylammonium chloride;
dioctylmethyl 2-butanoyloxyethylammonium bromide; and the like.

The quaternary bleach activators can be made by reacting halohydrocarbyl esters of carboxylic acids with trihydrocarbyl amines under conventional quaternary ammonium salt forming reaction conditions. This is shown by the following equation:

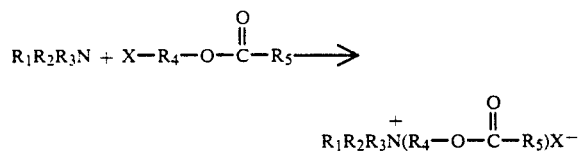

The preparation is shown in the following examples.

EXAMPLE 1

In a reaction vessel was placed 42.8 grams of 2-bromoethyl acetate, 58.9 grams of tetradecyldimethylamine and 107.6 grams of methylethyl ketone (MEK) solvent. The mixtures was refluxed (ca. 90° C.) under nitrogen with stirring for 7 hours. The reaction mixture was cooled and the solvent decanted leaving as the product tetradecyldimethyl 2-acetyloxyethylammonium bromide.

EXAMPLE 2

In a glass reaction vessel was placed 56.3 grams of didecylmethylamine, 32.3 grams of 2-bromoethyl acetate and 102 grams of MEK. The mixture was stirred under nitrogen at reflux (ca. 86° C.) for 6 hours. It was then cooled and allowed to stand overnight. In the morning, a crystalline precipitate had formed which was recovered by filtration. The precipitate was didecylmethyl 2-acetyloxyethylammonium bromide.

EXAMPLE 3

In a glass reaction vessel under nitrogen was placed 78.25 grams of ethyl acetate solvent and 32.65 grams of 2-bromoethyl acetate. While stirring, 41.14 grams of dodecyl dimethyl amine was added dropwise. A slight exotherm was observed. Heat was applied and the temperature raised to reflux (ca. 89° C.) which was continued for 6 hours. The mixture was then cooled to $-10°$ C. causing the product to precipitate. The product, dodecyldimethyl 2-acetyloxyethylammonium bromide, was recovered by filtration.

The novel bleach activators can also be made by first making a trihydrocarbyl hydroxyalkyl ammonium halide and then esterifying this by reaction with a carboxylic acid anhydride or acid halide. This is shown in the following two equations.

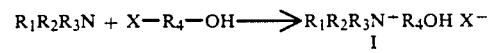

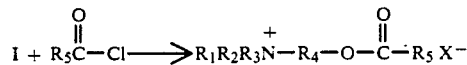

This synthetic method is shown in the following example.

EXAMPLE 4

In a reaction vessel was placed 13.14 grams of dodecyldimethyl 2-hydroxyethylammonium bromide, 21.22 grams of acetone solvent and 4.72 grams of sodium carbonate. While stirring under nitrogen, 3.27 grams of acetyl chloride was added dropwise. Gas evolution occurred. The mixture was then refluxed (ca. 60° C.) for 6 hours. The solvent was removed under vacuum. The residue was extracted with isopropanol to dissolve the quat and the solution was filtered hot to remove sodium chloride and sodium carbonate. The filtrate was evaporated under vacuum leaving as the product dodecyldimethyl 2-acetyloxyethylammonium bromide.

The bleach activators are used in combination with peroxygen bleaching compounds. These are compounds which are capable of forming hydrogen peroxide in aqueous solutions. Some examples of these are:
sodium perborate;
sodium perborate monohydrate;
sodium perborate tetrahydrate;
sodium carbonate peroxyhydrate;
sodium pyrophosphate peroxyhydrate;
urea peroxyhydrate;
sodium peroxide;
and the like including the other alkali metal salts of the above salt compounds. The more preferred bleaches are the sodium perborate hydrates.

The amount of bleach activator in the bleaching compositions is a function of the amount of peroxygen bleaching compounds. Preferably there should be at least a stoichiometric amount of bleach activator. This amount is 1 mole for each mole equivalent of active oxygen in the bleaching compound. A useful range is about 1-10 and more preferably 1-5 moles of bleach activator per each mole equivalent of active oxygen in the bleaching compound.

The bleaching composition can be packaged separately and added as required to the wash solution. More preferably the bleach composition is incorporated as part of the laundry detergent package which includes a surfactant. The surfactant can be one or more compatible surface active agents of the anionic, nonionic, zwitterionic, amphoteric or cationic types. Useful anionic surfactants include fatty acid soaps, alkali or ammonium salts of alkylbenzenesulfonic acids, alpha-olefin sulfonic acids and the like.

Nonionic surfactants include condensation products of alkylene oxides with organic hydrophobic compounds such as alkyl phenols or $C_{8-22}$ alcohols.

Zwitterionic surfactants include derivatives of $C_{8-18}$ aliphatic quaternary ammonium, phosphonium and sulfonium compounds. In fact the bleach activators of this invention also function as surfactants.

Laundry detergents usually include builders to remove certain metals from the laundry solution. Examples of these builders are sodium polyphosphates, sodium salts of ethylenediamine tetraacetic acid, sodium salts of nitrilotriacetic acid, natural and synthetic zeolites and the like. For environmental reasons the preferred builder is Zeolite A.

Other conventional laundry detergent components include suds boosters, suds suppressors, soil release agents, soil suspending agents, dyes, fillers, optical brighteners, germicides, perfumes, antioxidants, enzymes, buffering agents and the like.

A typical laundry detergent of this invention will contain about 1–30, preferably 5–15 weight percent surfactant, 5–35 weight percent Zeolite A builder, 1–20 weight percent peroxygen bleaching agent, at least a stoichiometric amount of bleach activator, fillers, and the like.

Tests were conducted which demonstrated the bleach activator properties of the invention. The test was adapted from A. H. Gilbert "Effective Bleaching with Sodium Perborate", Detergent Age, July, 1967, page 30. The test is based on the rate that a bleach solution converts iodide to iodine which is measured by titration with aqueous sodium thiosulfate to a colorless end point.

First a stock surfactant solution was prepared by placing 16.0 grams of sodium tripolyphosphate and 1.0 grams of sodium lauryl sulfate in a flask and diluting this with water to 1 liter. A 100 ml portion of the stock solution was then placed in a 250 ml flask and held at test temperature in a water bath. Then 0.18 grams of sodium perborate tetrahydrate (10.4 weight percent available oxygen, 1.17 milimoles available oxygen) was placed in the flask and at the same time the bleach activator in an amount equal to the moles of available oxygen was added. The time was recorded as "zero time". After a pre-set time, the test solution was quenched by adding 15 ml of glacial acetic acid and crushed ice. The quenched test solution was treated with several crystals of potassium iodide and then titrated with 0.1 molar aqueous sodium thiosulfate to a colorless end point. From this the amount of oxygen available at the quenched time could be calculated. The amount of oxygen made available by bleach activators of this invention at various quench times and temperatures is given in the following tables. Without any activator the available oxygen would be nil even at 120° F.

TABLE 1

| | Test at 90° F. | | | |
|---|---|---|---|---|
| | Available Oxygen (m moles) At Quench Time (min.) | | | |
| Activator | 5 | 7 | 10 | 15 |
| A. | $3.3 \times 10^{-5}$ | $3.4 \times 10^{-5}$ | $3.4 \times 10^{-5}$ | $2.1 \times 10^{-5}$ |
| B. | $9 \times 10^{-5}$ | $1.3 \times 10^{-4}$ | $1.0 \times 10^{-5}$ | $6.8 \times 10^{-5}$* |

*at 12 minutes

| | Test at 120° F. | | | | |
|---|---|---|---|---|---|
| | Available Oxygen (m moles) At Quench Time (min.) | | | | |
| Activator | 2 | 3 | 5 | 10 | 15 |
| A. | $2.9 \times 10^{-5}$ | $4.8 \times 10^{-5}$ | $2.9 \times 10^{-5}$ | $2.3 \times 10^{-5}$ | $1.1 \times 10^{-5}$ |
| B. | | $1.8 \times 10^{-4}$ | | $1.1 \times 10^{-4}$* | |
| C. | $1.0 \times 10^{-4}$ | | $1.6 \times 10^{-5}$ | $5.6 \times 10^{-6}$ | |

*at 7 minutes

Test Bleach Activators
A. didecylmethyl 2-acetyloxyethylammonium bromide
B. hexadecyldimethyl 2-acetyloxyethylammonium bromide
C. octyldimethyl 2-acetyloxyethylammonium bromide The tests show that the bleach activators of the invention are effective at temperatures as low as 90° F. In addition the present activators have surfactant, germicidal and fungicidal properties.

We claim:

1. A quaternary ammonium laundry bleach activator having the formula

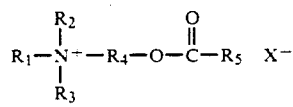

wherein $R_1$ and $R_2$ are alkyls containing 8–20 carbon atoms, $R_3$ is methyl, $R_4$ is $-(CH_2CH_2)-$, $R_5$ is an alkyl containing 1–20 carbon atoms and X is a monovalent anion.

2. A bleach activator of claim 1 wherein X is halogen.

3. A bleach activator of claim 2 wherein $R_5$ is an alkyl containing 1–11 carbon atoms.

4. A bleach activator of claim 3 namely, didodecylmethyl 2-acetyloxyethylammonium chloride.

5. A bleach activator of claim 3 namely, didecylmethyl 2-acetyloxyethylammonium chloride.

6. A bleach activator of claim 3 namely, dioctylmethyl 2-acetyloxyethylammonium chloride.

7. An oxygen bleaching composition comprising a peroxygen bleaching compound and a bleach activator having the formula

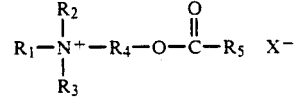

wherein $R_1$, $R_2$ and $R_3$ are aliphatic hydrocarbon groups containing 1–30 carbon atoms, $R_4$ is a divalent aliphatic hydrocarbon group containing 1–12 carbon atoms and $R_5$ is a hydrocarbon group containing 1–20 carbon atoms and X is a monovalent anion.

8. A bleaching composition of claim 7 wherein said inorganic peroxygen bleaching compound is selected from the group consisting of sodium perborate, sodium perborate hydrates, sodium carbonate peroxyhydrate, sodium pyrophosphate peroxygen hydrate, urea peroxyhydrate, sodium peroxide and mixtures thereof.

9. A bleaching composition of claim 7 wherein $R_1$ is an alkyl containing 8-20 carbon atoms, $R_2$ is an alkyl containing 8-20 carbon atoms or is a methyl group, $R_3$ is methyl, $R_4$ is $-(CH_2CH_2)-$, $R_5$ is an alkyl containing 1-20 carbon atoms and X is halogen.

10. A bleaching composition of claim 9 wherein $R_1$ is an alkyl containing from 8 to 20 carbon atoms, $R_2$ and $R_3$ are methyl, $R_4$ is $-(CH_2CH_2)-$ and $R_5$ is an alkyl containing 1-11 carbon atoms.

11. A bleaching composition of claim 10 wherein said bleach activator is hexadecyldimethyl 2-acetyloxyethylammonium chloride.

12. A bleaching composition of claim 10 wherein said bleach activator is tetradecyldimethyl 2-acetyloxyethylammonium chloride.

13. A bleaching composition of claim 10 wherein said bleach activator is dodecyldimethyl 2-acetyloxyethylammonium chloride.

14. A bleaching composition of claim 10 wherein said bleach activator is decyldimethyl 2-acetyloxyethylammonium chloride.

15. A bleaching composition of claim 10 wherein said bleach activator is dioctyldimethyl 2-acetyloxyethylammonium chloride.

16. A bleaching composition of claim 7 wherein $R_1$ and $R_2$ are alkyls containing 8-20 carbon atoms, $R_3$ is methyl, $R_4$ is $-CH_2CH_2-$ and $R_5$ is an alkyl containing 1-11 carbon atoms.

17. A bleaching composition of claim 16 wherein said bleach activator is didodecylmethyl 2-acetyloxyethylammonium chloride.

18. A bleaching composition of claim 16 wherein said bleach activator is didecylmethyl 2-acetyloxyethylammonium chloride.

19. A bleaching composition of claim 16 wherein said bleach activator is dioctylmethyl 2-acetyloxyethylammonium chloride.

20. A bleaching composition of claim 10 wherein said inorganic peroxygen compound is sodium perborate, a sodium perborate hydrate or mixtures thereof.

21. A bleaching composition of claim 16 wherein said inorganic peroxygen compound is sodium perborate, a sodium perborate hydrate or mixtures thereof.

* * * * *